US012274529B2

(12) United States Patent
Jordan et al.

(10) Patent No.: US 12,274,529 B2
(45) Date of Patent: Apr. 15, 2025

(54) SYSTEMS AND METHODS FOR IMAGING OF NEUROVASCULAR-COUPLING

(71) Applicant: Sheldon Jordan, Santa Monica, CA (US)

(72) Inventors: Sheldon Jordan, Pacific Palisades, CA (US); Taylor Kuhn, Marina Del Rey, CA (US); Sergio Becerra, Cambridge, MA (US)

(73) Assignee: Synaptec Network, Inc., Santa Monica, CA (US)

( * ) Notice: Subject to any disclaimer, the term of this patent is extended or adjusted under 35 U.S.C. 154(b) by 839 days.

(21) Appl. No.: 16/410,130

(22) Filed: May 13, 2019

(65) Prior Publication Data

US 2019/0357770 A1    Nov. 28, 2019

Related U.S. Application Data

(60) Provisional application No. 62/755,810, filed on Nov. 5, 2018, provisional application No. 62/670,512, filed on May 11, 2018.

(51) Int. Cl.
*A61B 5/00*     (2006.01)
*A61B 5/055*    (2006.01)
(Continued)

(52) U.S. Cl.
CPC .......... *A61B 5/0042* (2013.01); *A61B 5/055* (2013.01); *A61B 5/369* (2021.01); *A61B 5/4064* (2013.01);
(Continued)

(58) Field of Classification Search
CPC ....... A61B 5/0042; A61B 5/055; A61B 5/369; A61B 5/4064; A61B 5/6803;
(Continued)

(56) References Cited

U.S. PATENT DOCUMENTS

2003/0202596 A1* 10/2003 Lainema .............. H04N 19/521
                                                    375/E7.125
2007/0010732 A1   1/2007 DeYoe et al.
(Continued)

FOREIGN PATENT DOCUMENTS

CN      106580248 A    11/2016

OTHER PUBLICATIONS

Bestelmeyer et al. 2014 J. Neurosci. 34:8098-8105 (Year: 2014).*
(Continued)

*Primary Examiner* — Keith M Raymond
*Assistant Examiner* — Patrick M Mehl
(74) *Attorney, Agent, or Firm* — Fish IP Law, LLP

(57) ABSTRACT

Apparatus, systems, and methods for comparative analysis of tissue and organ scans between patients or groups of patients without sensitivity to patient-specific or scanner specific characteristics, including prediction, diagnosis, prognosis, tracking, and treatment guidance are disclosed. Blood oxygen level dependent (BOLD) fMRI is performed on a patient, and the resulting structural and functional data is preprocessed to remove artifacts and correct motion defects. A BOLD value is selected from the Vein of Galen as the maximum anatomically plausible intensity and from the Middle Cerebral Artery as the minimum anatomically plausible intensity. The maximum and minimum intensities are used to normalize the BOLD data and generate a neurovascular coupling statistical map of the brain.

17 Claims, 3 Drawing Sheets

(51) Int. Cl.

| | |
|---|---|
| *A61B 5/1455* | (2006.01) |
| *A61B 5/16* | (2006.01) |
| *A61B 5/369* | (2021.01) |
| *G01R 33/48* | (2006.01) |
| *G06T 7/00* | (2017.01) |

(52) U.S. Cl.
CPC .......... *A61B 5/6803* (2013.01); *G06T 7/0016* (2013.01); *A61B 5/1455* (2013.01); *A61B 5/165* (2013.01); *A61B 5/6814* (2013.01); *G01R 33/4806* (2013.01)

(58) Field of Classification Search
CPC ..... A61B 5/1455; A61B 5/165; A61B 5/6814; A61B 5/4076; G06T 7/0016; G01R 33/4806
See application file for complete search history.

(56) References Cited

U.S. PATENT DOCUMENTS

| | | | |
|---|---|---|---|
| 2017/0236294 A1* | 8/2017 | Fisher | G06T 7/0012 600/419 |
| 2017/0340260 A1 | 11/2017 | Chowdhury | |

OTHER PUBLICATIONS

Serwadda et al. 2015 IEEE 7th Internat. Conf. Biometrics Theory Applications and Systems pp. 1-7 (Year: 2015).*
Han 2012 Data Mining Concepts and Techniques 3rd Edition, Morgan Kaufmann Publication, 740 pages (Year: 2012).*
Hawezi 2015 PhD Thesis NeuroScience Nottingham University UK, 184 pages (Year: 2015).*
Wellcome Trust Center for Neuroimaging, Department of Cognitive Neurology, University College London, http://www.fil.ion.ucl.ac.uk/spm/ with http://web.archive.org/web/20180507050122/ and http://www.fhttp://web.archive.org/web/20180319113110/http://www.fil.ion.ucl.ac.uk/spm/software/spm8/ (Year: 2018).*
Hassan et al. 2016 Scientific Reports 6: article 25295, 9 pages (Year: 2016).*
Kampe 2014 MS Thesis Medical Radiation Physics Department Lund University Sweden, 43 pages (Year: 2014).*
Chupeau et al. 2000 Proc. SPIE 4067:884-893 (Year: 2000).*
Wikipedia 2017 Cerebral Circulation; internet address for archived reference https://web.archive.org/web/20170106101317/https://en.wikipedia.org/wiki/Cerebral_circulation (Year: 2017).*
Caballero-Gaudes et al. 2017 NeuroImage 154:128-149 (Year: 2017).*
Yen et al. 2018 NeuroImage 164:121-130; ePub. Date Mar. 2017 (Year: 2017).*
Golbabaci et al. 2016 23rd Iranian Conference on Biomedical Engineering and 2016 1st International Iranian Conference on Biomedical Engineering (ICBME) IEEE Xplore 6 pages (Year: 2016).*
Liu et al. 2017 Neuroimage 150:213â229 (Year: 2017).*

* cited by examiner

SYSTEMS AND METHODS FOR IMAGING OF NEUROVASCULAR-COUPLING

This application claims priority to U.S. provisional application 62/670,512, filed May 11, 2018 and U.S. provisional application 62/755,810, filed Nov. 5, 2018, the disclosures of which are incorporated herein by reference.

FIELD OF THE INVENTION

The field of the invention is methods, systems, kits, and devices related to tissue and organ imaging and analysis.

BACKGROUND

The background description includes information that may be useful in understanding the present invention. It is not an admission that any of the information provided herein is prior art or relevant to the presently claimed invention, or that any publication specifically or implicitly referenced is prior art.

Neurovascular coupling refers to the relationship between (1) activity of neurons, and (2) the supply of oxygen and nutrients local to the neurons as provided by nearby blood vessels. Attempts have been made in the prior art to measure and/or visualize neurovascular coupling ("NVC") using Electroencephalography ("EEG"), optical imaging, and functional magnetic resonance imaging ("fMRI"). However, these techniques all require comparing recordings of the brain at rest to recordings of the brain while it performs a task (e.g., visual task, holding breath, cognitively engaging task, etc). Moreover, each of these techniques is sensitive to patient-specific conditions (e.g., hydration, brain morphometry, blood pressure, blood oxygenation, etc) and scanner-specific conditions (e.g., model, software, sensitivity, environmental conditions, etc). As such, while patient and scanner specific analysis can be performed reliably, cross-analysis between different patients or cohorts cannot be performed reliably.

Thus, there remains a need for systems and methods for providing analysis between organ or tissue imaging that is not sensitive to patient-specific or scanner-specific characteristics.

SUMMARY OF THE INVENTION

The inventive subject matter provides apparatus, systems, and methods for comparative analysis of tissue and organ scans between patients or groups of patients without sensitivity to patient-specific or scanner specific characteristics, including prediction, diagnosis, prognosis, tracking, and treatment guidance.

The inventive subject matter contemplates apparatus, systems, and methods of measuring and visualizing neurovascular coupling using fMRI without the requirement of measuring and comparing patient brain activity during a task with patient brain activity during rest. The variability of blood-oxygen-level dependent ("BOLD") contrast image fMRI signals are measured by comparing a resting BOLD fMRI against an anatomically plausible variability range. Surprisingly, such inventive systems and methods enable assessment of neurovascular coupling with significantly improved spatial resolution, while simultaneously controlling for differences not only between patients, but also across different MM scanners. Such methods provide unprecedented robustness, reliability, and reproducibility.

Systems are contemplated for analyzing a substrate-dependent activity (e.g., BOLD activity, glycolysis, etc.) in a tissue (e.g., brain). Such systems have a scanner or detector (e.g., MRI, fMRI) that detects signals related to the substrate-dependent activity. While the signals can be of different types (e.g., oxygen related, metabolic activity related, metabolite related, blood flow related, enzymatic activity related, etc), or from different sources (e.g., different regions of the brain, etc), preferably the signals are of the same type. A computer processor is informationally coupled to the scanner to process data from the scans, including organizing the signals into data sets, and applying refining applications (e.g., cleaning, motion correcting, etc) to the data set to produce a refined data set. Refined data sets are used to identify maximum and minimum values within each data set, which are used to normalize at least some of the values in the refined data set.

As an example when measuring BOLD activity in the brain, the maximum value is derived from the Circle of Willis (or Vein or Galen, etc), and the minimum value is derived from the Sagittal Sinus (or Middle Cerebral Artery (MCA), etc). It should be appreciated that, when dealing with imaging scanners, the data is typically stored as a plurality of voxels. To normalize such data sets, it is contemplated that the maximum value is the mean of resting BOLD values from a first subset of voxels in the Circle of Willis (or Vein or Galen, etc), and the minimum value is the mean of resting BOLD values from a second subset of voxels in the Sagittal Sinus (or MCA, etc). Viewed from another perspective, the maximum value and the minimum value define an (anatomically) plausible range of values that the computer processor uses to normalize the refined data set. It is also contemplated that only the first subset of voxels in the Circle of Willis (or Vein or Galen, etc) is used to set the maximum value, only the second subset of voxels in the Sagittal Sinus (or MCA, etc) is used to set the minimum value, or vice versa.

Systems for visualizing BOLD activity in the patient's brain are also contemplated, involving fMRI generating BOLD contrast data sets that are refined and analyzed to identify maximum and minimum values in the refined data set. The maximum and minimum values are used to normalize at least part (preferably all) of the refined data set, which is then depicted by a display informationally coupled to the system.

Methods are also contemplated, including methods for normalizing a data set made up of a plurality of signal data. A maximum value and a minimum value are identified in the plurality of signal data and used to define a plausible range of values. The plausible range of values is then used to normalize the data set. It should be appreciated that data sets that are not normalized offer little comparative analytical value, while normalized data sets can favorably be used to compare data between different patients, taken at different times, by different scanners, under different conditions.

Contemplated methods include diagnosing a condition in a patient, where the patient's data set is accessed and analyzed to identify a maximum value and a minimum value. The maximum and minimum values are applied to the patient's data set to produce a normalized data set, which is then compared with a profile of the condition and used to diagnose the condition in the patient. In preferred embodiments, the profile is a normalized profile of at least one different patient representative of the condition, more preferably an average of a plurality of normalized profiles. While it is contemplated the inventive subject matter is applicable to any condition (e.g., disease, disorder, characteristic, etc) that is related to a detectable profile, preferred conditions related to the brain include those listed in Table 1.

TABLE 1

| Condition | Profile |
| --- | --- |
| Alzheimer's disease: | Irregular neurovascular coupling in the hippocampus and surrounding cortex |
| Parkinson's disease: | Irregular neurovascular coupling in the substantia nigra and basal ganglia |
| Vascular dementia: | Irregular neurovascular coupling diffusely throughout the brain |
| MS: | Irregular neurovascular coupling focally around MS lesions |
| Cancer: | Increased neurovascular coupling around the tumor and decreased coupling in surrounding necrotic tissue |
| Schizophrenia: | Irregular neurovascular coupling in the frontal lobe as well as heschl's gyrus |
| Depression: | Irregular neurovascular coupling in the frontal lobe |
| Substance abuse: | Irregular neurovascular coupling in the diffusely throughout the cortex but likely not in subcortical structures |
| Traumatic Brain Injury: | Reduced neurovascular coupling near area of injury |

Methods are also contemplated for tracking a condition in a patient, where the patient's data set, including a first data set recorded at to and a second data set recorded at $t_1$, is accessed to identify a maximum and minimum value in each of the first and second data sets. The maximum and minimum values are applied respectively to the first and second data sets to produce normalized first and second data sets, which are then compared with a profile of the condition in order to track the condition in the patient. Preferably the profile is one of (1) a normalized profile or (2) an average of a plurality of normalized profiles representative of the condition.

Methods are also contemplated for predicting a condition in a patient, where the patient's data set is accessed to identify a maximum and minimum value, which is then applied to the patient data set to produce a normalized data set. The normalized data set is then compared with a predictive profile of the condition to predict the condition in the patient. Preferably, the predictive profile is one of (1) a normalized predictive profile or (2) an average of a plurality of normalized predictive profiles representative of the condition.

Prognosis methods are also contemplated, where a patient's data set is accessed to identify a maximum and minimum value and applied to the patient data set to produce a normalized data set. The normalized data set is then compared with a plurality of prognosis profiles of the condition to prognose the condition in the patient. Preferably the plurality of prognosis profiles include one or more of (1) a condition-stable profile, (2) a condition-progressing profile, (3) a condition-receding profile, (4) a condition-terminal profile, or (5) an average of a plurality of normalized prognosis profiles representative of the condition.

Methods of guiding treatment of a condition in a patient are also contemplated, where the patient's data set, including a pre-treatment data set and a post-treatment data set, is accessed to identify a maximum and minimum value in each of the pre-treatment and post-treatment data sets. The maximum and minimum values are applied respectively to the pre-treatment and post-treatment data sets to produce normalized pre-treatment and post-treatment data sets. The normalized pre-treatment and post-treatment data sets are compared with a desirable profile of the condition to guide subsequent treatment of the patient. Preferably the desirable profile is one of (1) a normalized condition-stable profile, (2) a normalized condition-receding profile, (3) a normalized condition-free profile, or (4) an average of a plurality of normalized desirable profiles of the same type.

It is also contemplated that methods of terminating treatment of a condition in a patient include accessing a patient's data set including a pre-treatment data set and a post-treatment data set. Maximum and minimum values in each of the pre-treatment and post-treatment data sets are identified and applied respectively to the pre-treatment and post-treatment data sets to produce normalized pre-treatment and post-treatment data sets. The normalized data sets are then compared with a condition-free profile of the condition to indicate terminating treatment. Preferably the condition-free profile is one of (1) a normalized condition-free profile or (2) an average of a plurality of normalized condition-free profiles.

Methods of predicting (alternatively diagnosing) a condition in a specific patient are also contemplated, where a patient-specific data set and a plurality of non-patient-specific data sets related to the condition are accessed. Maximum and minimum values in at least some of the non-patient-specific data sets are identified and applied to each respective data set in the plurality of non-specific data sets to produce a plurality of normalized non-patient-specific data sets. The normalized non-patient-specific data sets are then used to train a machine learning algorithm to predict the condition, producing a predictive (or diagnosing) algorithm, which can then be applied to the patient-specific data set to predict (or diagnose) the condition in the specific patient.

Methods are also contemplated for prognosing a condition in a specific patient by accessing a patient-specific data set and a plurality of non-patient-specific data sets related to the condition and identifying a maximum value and a minimum value in at least some of the non-patient-specific data sets. The maximum and minimum values are applied to each respective non-specific data set to produce a plurality of normalized non-patient-specific data sets, which can be used to train a machine learning algorithm to prognose the condition, producing a prognosis algorithm. The prognosis algorithm is then applied to the patient-specific data set to prognose the condition in the specific patient. Preferably, the plurality of non-patient-specific data sets comprise at least one of (1) a plurality of condition-stable data sets for a single patient, (2) a plurality of condition-progressing data sets for a single patient, (3) a plurality of condition-receding data sets for a single patient, or (4) a plurality of condition-terminal data sets for a single patient. Viewed from another perspective, data sets for a single patient can be collected from $t_0$, preceding the condition, through $t_i$, the occurrence of the condition, to $t_n$, where n>i.

Methods of guiding treatment of a condition in a specific patient are also contemplated. A patient-specific data set and a plurality of non-patient-specific data sets related to a desirable response to treatment of the condition are accessed. A maximum and minimum value in at least some of the non-patient-specific data sets are identified and applied to each respective non-patient-specific data set to produce a plurality of normalized non-patient-specific data sets. A machine learning algorithm is then trained on normalized non-patient-specific data sets to guide treatment, producing a guiding algorithm. The guiding algorithm is then applied to the patient-specific data set to guide treatment of the condition in the specific patient. Preferably, the plurality of non-patient-specific data sets comprise at least one of (1) a plurality of condition-stable data sets for a single patient, (2) a plurality of condition-receding data sets for a single patient, or (3) a plurality of condition-free data sets for a single patient. Optionally, the patient-specific data set comprises a pre-treatment data set and a post-treatment data set.

Methods are also contemplated for training a machine learning algorithm on a plurality of patient data related to a condition. The plurality of patient data related to the condition is accessed and to identify a maximum and minimum value in each set of data. The maximum and minimum values are applied respectively to each data set in the plurality of data sets to produce a plurality of normalized patient data. The machine learning algorithm is then trained on the plurality of normalized patient data to predict, diagnose, prognose, or propose treatment for the condition. Viewed from another perspective, a prediction device, a diagnosis device, a prognosis device, a treatment device, or some combination thereof, is produced by the inventive subject matter capable of predicting, diagnosing, prognosing, or treating a condition based on review of patient data related to the condition, for example BOLD fMRI data.

Systems are also contemplated for analyzing a condition-related signal in a tissue. A sensor is used to detect a plurality of condition related signals in the tissue and a processor informationally coupled with the sensor organizes the plurality of signals into a data set, identifies a maximum and minimum value within the data set, and uses the maximum value and the minimum value to normalize at least some of the values in the data set. Preferably, before identifying the maximum and minimum value within the data set, the computer processor applies a first refining application to the data set to produce a refined data set.

Systems for providing an analysis of a condition in a specific patient are also contemplated. A display is informationally coupled to a computer processor to depict the analysis. The computer processor has at least partial access to a patient-specific data set and a plurality of non-patient-specific data sets related to the condition. The computer processor identifies a maximum value and a minimum value in at least some of the data sets in the plurality of non-patient-specific data sets and applies the maximum and minimum values to each respective data set in the plurality of non-specific data sets to produce a plurality of normalized non-patient-specific data sets. The plurality of normalized non-patient-specific data sets are applied to train a machine learning algorithm to analyze the patient-specific data set with respect to the condition, producing an analytical algorithm. The analytical algorithm is then applied to the patient-specific data set to provide the analysis of the condition in the specific patient. Preferably, the analysis is at least one of a prediction, a diagnosis, a prognosis, or a proposed treatment of the condition in the specific patient.

Systems for providing normalized data for analysis are also contemplated. A display implement (e.g., monitor, projector, augmented reality device, virtual reality device, printer, 3D printer, etc), is informationally coupled to a computer processor to present (e.g., render, etc) the normalized data. The computer processor preferably has at least partial access to a patient-specific data set and a plurality of non-patient-specific data sets related to a condition. The computer processor identifies a maximum value and a minimum value in at least some of the data sets in the plurality of non-patient-specific data sets and applies the maximum and minimum values to each respective data set in the plurality of non-specific data sets to produce a plurality of normalized non-patient-specific data sets. At least some of the plurality of normalized non-patient-specific data sets are presented by the display implement. It is contemplated the presentation can be of each discrete data set, a (preferably weighted) combination of multiple data sets, an average of some (preferably most, more preferably all) data sets, or other appropriate statistical combinations of data sets. The analysis is preferably performed by a trained reader, for example a neurologist, a radiologist, a psychiatrist, etc, but can also be performed by an artificial trained reader, for example an artificial intelligence, and trained machine learning algorithm, etc. Preferably, the analysis is at least one of a prediction, a diagnosis, a prognosis, or a proposed treatment of the condition in the specific patient.

Various objects, features, aspects, and advantages of the inventive subject matter will become more apparent from the following detailed description of preferred embodiments, along with the accompanying drawing figures in which like numerals represent like components.

DETAILED DESCRIPTION

Figure 1:
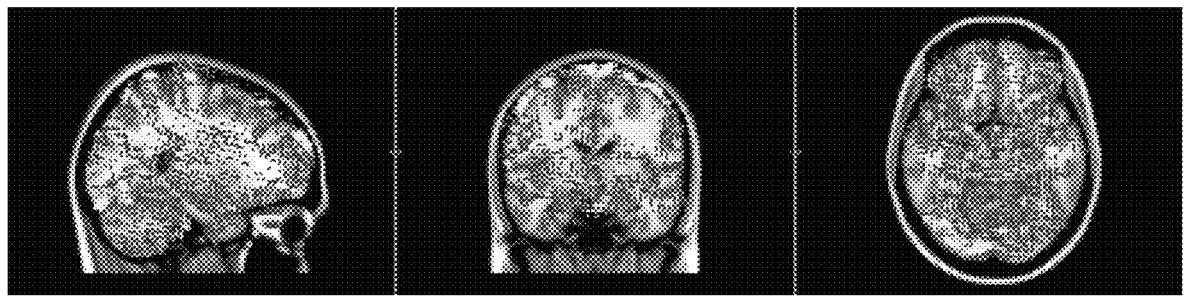
FIG. 1 shows BOLD contrast fMRI of a healthy adult brain.

The inventive subject matter provides apparatus, systems, and methods for comparative analysis of tissue and organ scans between patients or groups of patients without sensitivity to patient-specific or scanner specific characteristics, including prediction, diagnosis, prognosis, tracking, and treatment guidance.

Structural and functional data is acquired using scanners known in the art, for example a 1.5 T Siemens Espree scanner with a 16-channel head coil. Structural images are preferably acquired in high spatial resolution to properly align subject data to standard atlas space. For example, suitable structural data includes a magnetization-prepared, rapid-acquisition gradient-echo (MPRAGE) T1-weighted sequence (TR=1810 ms; TE=3.50 ms; FoV=180×240 mm; resolution 1 mm isotropic), though additional or alternative structural data is contemplated as appropriate. BOLD/functional images are taken for about 8 minutes and 20 seconds long, but can be 5 to 8 minutes long, less than 4, 3, 2, or 1 minute long, or greater than 10, 15, or 20 minutes long. Functional sequences are preferably acquired while the subject rests (e.g., TR=2500 ms; TE=30 ms; FoV=192×192 mm; resolution 4 mm isotropic; 200 spatial volumes).

Preferably, data recorded for each patient, for example fMRI data, is pre-processed to improve analysis, for example using tools from the FMRIB Software Library. It is contemplated that preprocessing reduces noise, for example, such that there is an increase in sensitivity and validity of analysis. However, additional preprocessing steps with various results are contemplated. For example, imaging related to the brain such as fMRI data is preferably "de-faced" or "skull stripped" (e.g., via MCFLIRT) to produce an image showing primarily the cerebrum, cerebellum, brain stem and cerebrospinal fluid ("CSF") spaces. Data can also (or alternatively) be motion corrected (e.g., via high pass filter, etc), spatially smoothed (e.g., 5 mm FWHM, etc) or registered to standard space (e.g., via non-linear warping methods, etc). Optionally, further nefarious motion artifact can be corrected, for example by Independent Component Analysis strategy for Automatic Removal of Motion Artifact (ICA-AROMA)

With respect to motion correction, it is contemplated MRI imaging modalities acquire a series of images, for example once every few seconds over a period of minutes, multiple times per second over a series of minutes, etc. Preferably statistical analysis is applied to unprocessed imaging results to extract useful information. While the assumption that any given voxel represents the same location in the brain over the course of the scan can be used, it is preferred that additional (or alternative analysis) be applied as subjects typically move during their scans, especially during the longer ones.

In some embodiments, it is desirable to correct data to remove imperfections, artifacts, or corrupted data. For example, optionally correcting MRI data for patient motion can be viewed in terms of image registration and spatial alignment of brain images. For example, image registration is characterized by minimizing the difference between a reference image and a floating image (e.g., calculating differences using a cost function, etc). The MRI data to be corrected for motion are preferably acquired using the same scanning parameters and on the same subject, thus making the transformations both intramodal and intrasubject. Under this analysis, motion correction is comprised of rigid body transformations.

While all appropriate statistical analysis or data correction methods are contemplated, preferably cost functions applying normalized cross correlation are used. In mathematical terms, the inner product of the normalized reference image A, with the normalized floating image B, such that $$\text{COST} = \left\langle \frac{A}{\|A\|}, \frac{B}{\|B\|} \right\rangle.$$

Preferred motion corrections utilize rigid body transformations with six (6) different parameters to optimize; three (3) translations and three (3) rotations. Minimizing the difference between the floating and reference image requires searching for the transformation by scanning through the different parameters and calculating the cost. In preferred embodiments, finding the transformation starts with a coarse search through the rotation, followed by optimizing more finely for translations. The coarse search broadly localizes the areas that lead to a minimized difference between images. The finer search is done over the localized regions to further pinpoint the minima. A full optimization can further be done for each local minima from the finer search.

Correcting MRI data for motion can raise complications, for example (1) local minima leading to a misalignment, and (2) time cost to find the absolute minimum. Surprisingly, separate assumptions can be made to safely remedy such issues without biasing the data. For example, subsampling across the whole set of MRI data, or for each image, allows for a coarser and computationally faster search to show the general area of the absolute minima, providing the technical effect of substantially reduced computational stress or costs for compute hardware. The subsampled registration is preferably used to initialize searches at higher resolution. Additionally (or alternatively), an assumption can be made that motion between successive or chronological images will be small. Once the transformation for a first image or pair of images has been determined, that transformation is used to initialize the search for the subsequent image, favorably reducing time and cost of analysis. In preferred embodiments, both assumptions (subsampling and successive analysis) are applied to significantly optimize performance while surprisingly improving accuracy.

As a further example, motion correction begins by subsampling the set of images and picking the reference, typically the middle or median image. Every image in the series is then registered to the reference. Then, using the transformations from the subsampled set, the process is done on the full resolution series. The final stage builds off of the previous step by doing the search again, however more in depth (e.g., higher resolution, etc), and initialized by the transformations of previous. In addition to producing a series of images with noticeably improved motion correction, the transformations in the analysis describe both the relative motion between images, and when concatenated, the absolute motion from the reference image.

Aligning the fMRI series with motion correction is the first step in preparing the data. Preferably, the next step is to remove the artifactual signals that arise from motion, diminishing the strength of effects and findings being looked for. While removing afflicted volumes may achieve this goal, it also affects the temporal integrity of the sequence and decreases the degrees of freedom ("DOF"). A far more robust, and effective, method is to break the acquisition into separate components through an independent components analysis (ICA). From here, using the motion parameters gathered from motion correction, components with significant correlation to motion may be regressed out. This allows for the data to retain its temporal structure and successfully conserves DOF's while mitigating harmful motion artifact.

Using a standard atlas, manually drawn masks were created to capture voxels known to comprise the Circle of Willis as well as the Sagittal Sinus. However, additional atlases are contemplated, for example a patient-specific atlas, a demographic-specific atlas, a physician or trained professional developed atlas, etc. Further, while the Circle of Willis and the Sagittal Sinus were targeted regions, it is contemplated that other regions in the brain with relative differences in local blood oxygen levels can be used, for example the Vein of Galen and the Middle Cerebral Artery (MCA). This mask was created such that all voxels in the known region of interest were collected and then an erode function was used to remove the outer layer of voxels. In so eroding the mask, a single voxel gap was created between the mask and surrounding regions. This ensured that no extraneous regions were captured in the masks, as could be the case due to partial voluming or averaging during acquisition and/or registration.

After preprocessing was completed, the voxelwise time series mean of the resting-state fMRI data was computed. Then, using the previously generated masks, the mean resting BOLD value was extracted from voxels in the Circle of Willis (or Vein or Galen, etc) as well as from voxels within the Sagittal Sinus (or MCA, etc). The Circle of Willis (or Vein or Galen, etc) mean was used as the maximum anatomically plausible intensity while the sagittal sinus (or MCA, etc) mean represented the minimum anatomically plausible intensity. A total plausible signal variability range was then computed by subtracting the sagittal sinus (or MCA, etc) mean from the Circle of Willis (or Vein or Galen, etc) mean signal intensity value.

Next, the time series range for each voxel was computed by subtracting each voxel's time series minimum from its time series maximum. Alternative or additional methods are also contemplated, for example computing the time series range for each voxel first clipping the time series to a 90% winsorization (or 70%-90%, 90%-100%, etc) on a voxelwise level (or voxel pair, more than 3 voxels, more than 5 voxels, etc). Finally, the voxelwise time series range was divided by the total plausible range resulting in a ratio of the voxelwise to anatomically plausible variability. This final, voxelwise variability ratio was considered the resting BOLD-based proxy for neurovascular coupling (NVC). This method is robust to changes in general cerebrovascular health as it uses a within-patient approach to normalize signal intensity based on the patient's own cerebrovascular signal. However, it is limited in its sensitivity to BOLD signal variability.

Further steps are also contemplated, for example producing a measure of neurovascular response by using Gaussian mixture model effects segmentation. The histogram is treated as a bimodal distribution, allowing segmentation to split into two separate Gaussian curves. The first, larger distribution corresponds to the data of interest (and also in an anatomically plausible range) while the second targets voxels susceptible to noise, nefarious artifact, and regions not of interest. This produces a cleaned image of the neurovascular response.

Figure 2:
FIG. 2 shows BOLD contrast fMRI of a brain with mild neurocognitive disorder due to Alzheimer's Disease.
Figure 3:
FIG. 3 shows BOLD contrast fMRI of a brain with major neurocognitive disorder due to Alzheimer's Disease.

FIGS. 1-3 are examples of NVC results using this technique in a healthy adult (FIG. 1), an adult with mild amnestic neurocognitive disorder due to Alzheimer's disease (FIG. 2), and an adult with major neurocognitive disorder due to Alzheimer's disease (FIG. 3). For patients in FIGS. 2 and 3, Alzheimer's disease was verified using spinal tap-derived cerebrospinal fluid quantification of amyloid beta and phosphotau levels.

The same method as above was used with one modification. Rather than compute the voxelwise time series mean and extract the total range of signal intensity, the variance of the time series within each voxel was used as the metric of interest. Thus:

After processing was complete, using the previously generated masks, the standard deviation of the BOLD value was computed for the Circle of Willis (or Vein or Galen, etc) and the Sagital Sinus (or MCA, etc). The Circle of Willis (or Vein or Galen, etc) standard deviation was used as the maximum anatomically plausible variability while the sagittal sinus (or MCA, etc) standard deviation represented the minimum anatomically plausible variability. These standard deviations were squared to compute variance for the Circle of Willis (or Vein or Galen, etc) and Sagital Sinus (or MCA, etc), respectively. A total plausible signal variability value was then computed by subtracting the sagittal sinus (or MCA, etc) variance from the Circle of Willis (or Vein or Galen, etc) signal variance value.

Next, the time series variance for each voxel was computed by squaring each voxel's time series standard deviation. Finally, the voxelwise time series variance was divided by the total plausible variance resulting in a ratio of the voxelwise to anatomically plausible variance. This final, voxelwise variance ratio was considered another resting BOLD-based proxy for neurovascular coupling (NVC). This method is more sensitive to BOLD variability than the previous method. However, it is also somewhat limited by general cerebrovascular health confounds which could affect the range of variability of signal seen in the Circle of Willis (or Vein or Galen, etc) and the Sagittal Sinus (or MCA, etc).

It is contemplated that, due to unfavorable susceptibility to artifact inherent in fMRI data acquisition which can deleteriously affect the signal in the Vein of Galen (or Circle of Willis, etc) region, an alternate anatomical source can be isolated for the oxygenated signal intensity used for the maximum plausible signal. Preferably, such a region must provide the ability to measure signal from an artery in a robust and reliable manner. For this purpose, methods of the inventive subject matter can be further modified, altered, or enhanced.

For example, instead of using a Vein of Galen (or Circle of Willis, etc) mask, a mask of the Insula was generated which captured the MCA. Likewise, rather than (or in addition to) using the mean intensity or the variance of the intensity of all voxels within each mask (or groups or pairs of voxels), the value of the voxel with the highest signal intensity from within each mask can be used as the reference value for that region. This allows for more precise anatomical localization of arteries and veins within the BOLD signal, allowing for more anatomically precise determination of the anatomically plausible signal range.

After generating the time series mean for each voxel (or pair, or group of voxels) in the brain, the resting BOLD voxel intensity value can be extracted from the voxel with the highest signal intensity value in the Insula as well as from the voxel with the highest signal intensity value within the MCA (or sagittal sinus, etc). The highest intensity value from the Insula/MCA (or sagittal sinus, etc) is used as the maximum anatomically plausible intensity while the highest intensity value from the MCA represented the minimum anatomically plausible intensity. A total plausible signal intensity range can be computed by subtracting the MCA highest intensity from the insula/middle cerebral artery highest intensity value.

The voxelwise range (for example, computer as described above) can be further divided by the total anatomically plausible signal intensity. The resulting voxelwise signal intensity ratio is another resting BOLD-based proxy for neurovascular coupling (NVC). Preferably, such methods normalize the data across patients and across scanning platforms. This method is more sensitive to accurately detecting BOLD signal in arteries, thereby more accurately computing the anatomically plausible BOLD signal range. This method is also less affected by susceptibility to artifacts. Further improvements to the inventive methods are contemplated to improve or mitigate susceptibility to outliers in the data.

Registration to standardized space allows for visual and statistical comparison between groups or between patient and normative sample. Because these NVC metrics were computed at the voxel level, they could then be visualized with high spatial sensitivity. Further, due to the patient-specific anatomically plausible variability normalization method used, the final NVC image was not confounded by imaging environment-specific variables (e.g. scanner type, acquisition parameters) nor was it confounded by patient-specific variables (e.g. hydration status). This allowed for statistical comparison of NVC results across participants, including across participants collected on different data collection platforms (e.g. MR scanners).

It is further contemplated that methods and systems of the inventive subject matter be used to successfully predict, diagnose, or track a variety of conditions (e.g., diseases, etc) in various tissues or organs of a patient (e.g., brain tissue, brain etc). As an example, Table 1 identifies a number of conditions along with the respective signal profile of BOLD activity (or alternative indication of neurovascular coupling) that can be used to predict, diagnose, or track each condition.

Validation of methods and systems of the inventive subject matter was completed using proprietary data from patients. Resting BOLD functional MM data and images were preprocessed and then analyzed using inventive methods. Twenty Alzheimer's disease (mean age=76.88, sd=7.68 years; 50% female) patients were identified using the gold standard lumbar puncture amyloid-beta and tau markers. Twenty three healthy age- and sex-matched control participants were also recruited (mean age=68.34, sd=12.84; 50% female). A double blinded classification test was created to ensure that findings from this analysis are detectable by trained clinicians. In a blinded study, two clinicians were shown 3 normal and 3 AD subjects. Based on these 6 training cases, the clinicians created an agreed upon metric to classify the rest of the sample. The clinicians were independently presented 10 AD and 10 controls in a randomized order, and using their previously defined metric they classified 20 cases. Using the statistical NVC maps generated, the clinicians were able to classify patients accurately with 90% sensitivity, 80% specificity, 82% positive predictive value (PPV) and 89% negative predictive value (NPV). There was a 75% overlap between raters with regards to how they classified patients' diagnosis. See Table 2.

TABLE 2

|  | Sensitivity | Specificity | PPV | NPV | Agreement |
|---|---|---|---|---|---|
| Normal vs Alzheimer's | 90% | 80% | 82% | 89% | 75% |

A large external dataset was also used to cross-validate applying the inventive subject matter to differentiating patients based on level of neurocognitive impairment. The Open Access Series of Imaging Studies (OASIS) dataset was chosen based on its robust MRI repository and its classification of participants' level of cognitive proficiency. Classification of degree of cognitive impairment within the OASIS dataset was determined using Clinical Dementia Rating Scale (CDR). CDR level 0 corresponded to "no cognitive impairment" (N=1310, mean age=68.9, sd=9.32, 58.9% female); CDR level 0.5 corresponded to "mild cognitive impairment" (N=277, mean age=75.1, sd=7.38, 43.4% female); CDR level 1 corresponded to "mild dementia" (N=95, mean age=74.8, sd=8.37, 44.0% female). While CDR was used in this case, the inventive subject matter can be used in conjunction with other neurological or cognitive scales or metrics (e.g., Global Deterioration Scale, Dementia Severity Rating Scale, FAST scale, ABC Dementia Scale, etc), as well as patients that have not yet been scored or evaluated. For example, the inventive subject matter can be applied to validate a score, to validate methodologies for assigning scores, or assess accuracy of a score, as well as to assign scores or diagnoses.

Resting BOLD functional Mill images from the OASIS dataset were preprocessed and then analyzed with methods, systems, and devices of the inventive subject matter. Surprisingly, based on neurovascular coupling imaging and data alone, patients with CDR level 0 were accurately classified as CDR level 0 with 96.7% sensitivity, 100% specificity, 100% PPV and 97.1% NPV. Patients with CDR level 0.5 were accurately classified as CDR level 0.5 with 94.1% sensitivity, 97% specificity, 86.5% PPV and 98.8% NPV. Patients with CDR level 1 were accurately classified as CDR level 1 with 97.1% sensitivity, 98.5% specificity, 97.1% PPV and 98.5% NPV. See Table 3.

TABLE 3

|  | Sensitivity | Specificity | PPV | NPV |
|---|---|---|---|---|
| CDR 0 | 97.0 | 100.0 | 100.0 | 97.1 |
| CDR 0.5 | 94.1 | 97.0 | 86.5 | 98.8 |
| CDR 1 | 97.1 | 98.5 | 97.1 | 98.5 |

With regard to predicting cognitive decline in the future, the OASIS dataset was divided into those participants who were cognitively stable and those participants who displayed cognitive decline over time. The cognitively stable group was generated by selecting those participants who were initially classified by OASIS as CDR level 0 and who were followed for at least three years and did not demonstrate any change in CDR level (N=503, mean age=66.85, sd=8.46, 62% female). The cognitively declining group was generated by selecting those participants who were initially classified by OASIS as CDR level 0 and then converted to CDR level 0.5 or CDR level 1 later in the longitudinal study (N=400, mean age=75.03, sd=7.85, 53.7% female).

Resting BOLD functional Mill images from the OASIS dataset were processed and then analyzed with methods, systems, and devices of the inventive subject matter. Surprisingly, participants were accurately classified as CDR0 cognitive stable or CDR0 cognitive declining with 61% sensitivity, 62% specificity, 56% PPV and 67% NPV. See Table 4.

TABLE 4

|  | Sensitivity | Specificity | PPV | NPV |
|---|---|---|---|---|
| Stable Vs Declining | 61% | 62% | 56% | 67% |

Finally, the cognitively stable group was modified to include only those participants who had an amyloid positron emission tomography (PET) scan that was negative for amyloid. Amyloid detection was calculated using the Standardized Uptake Value ratio (SUVr) and the Binding Potential (BP), both of which are metrics derived from the amyloid binding ligand used during the PET scan. The lentil scale is a metric which incorporates both SUVr and BP to determine the likelihood a patient with certain amyloid PET metrics is normal or has Alzheimer's disease. A lentil scale of 0 is indicative of low likelihood of developing Alzheimer's disease. Therefore, this final sample of cognitive stable participants was determined based on those participants that did maintained a CDR value of 0 over at least three years and had a lentil score of less than 0. This final sample was comprised of CDR0 and amyloid PET-defined cognitively stable participants (N=188, mean age=63.83, sd=9.13, 58.5% female) and those participants who were initially classified by OASIS as CDR level 0 and then converted to CDR level 0.5 or CDR level 1 later in the longitudinal study (N=400, mean age=75.03, sd=7.85, 53.7% female).

Resting BOLD functional Mill images from the OASIS dataset were processed and then analyzed with methods, systems, and devices of the inventive subject matter. Surprisingly, participants were accurately classified as CDR0 cognitive stable or CDR0 cognitive declining with 71% sensitivity, 50% specificity, 75% PPV and 45% NPV. See Table 5.

TABLE 5

| | Sensitivity | Specificity | PPV | NPV |
|---|---|---|---|---|
| Stable Vs Declining | 71% | 50% | 75% | 45% |

Figure 4:
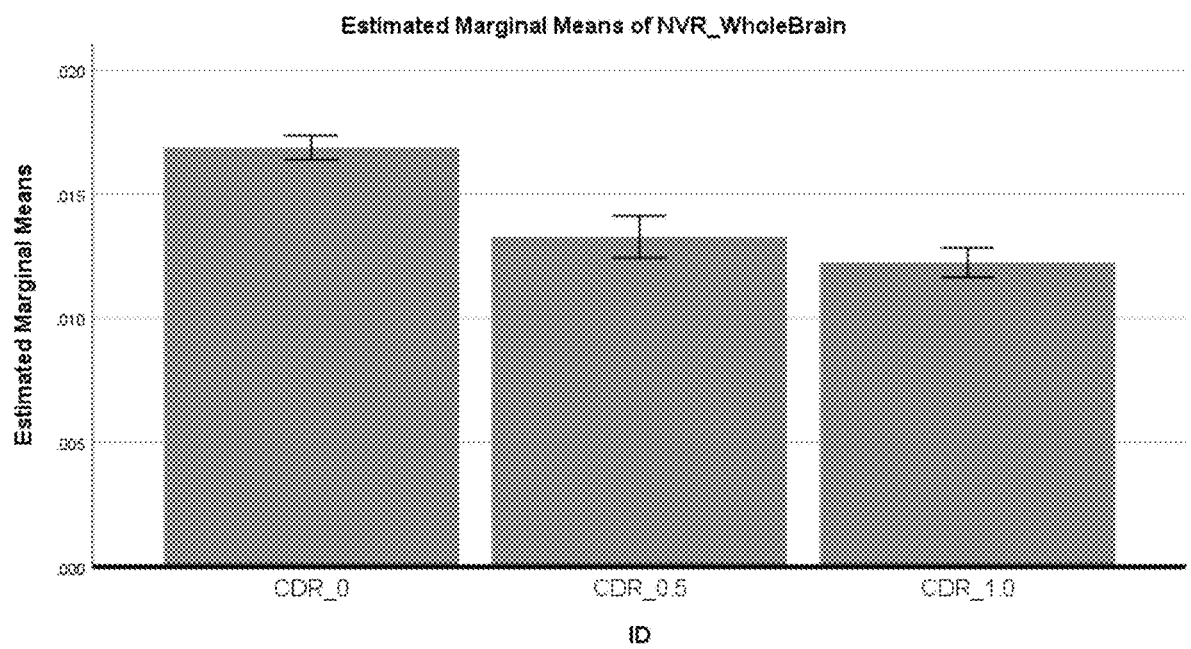
FIG. 4 shows results for patients with CDR 0, CDR 0.5, and CDR 1 for whole brain NVC.
Figure 5:
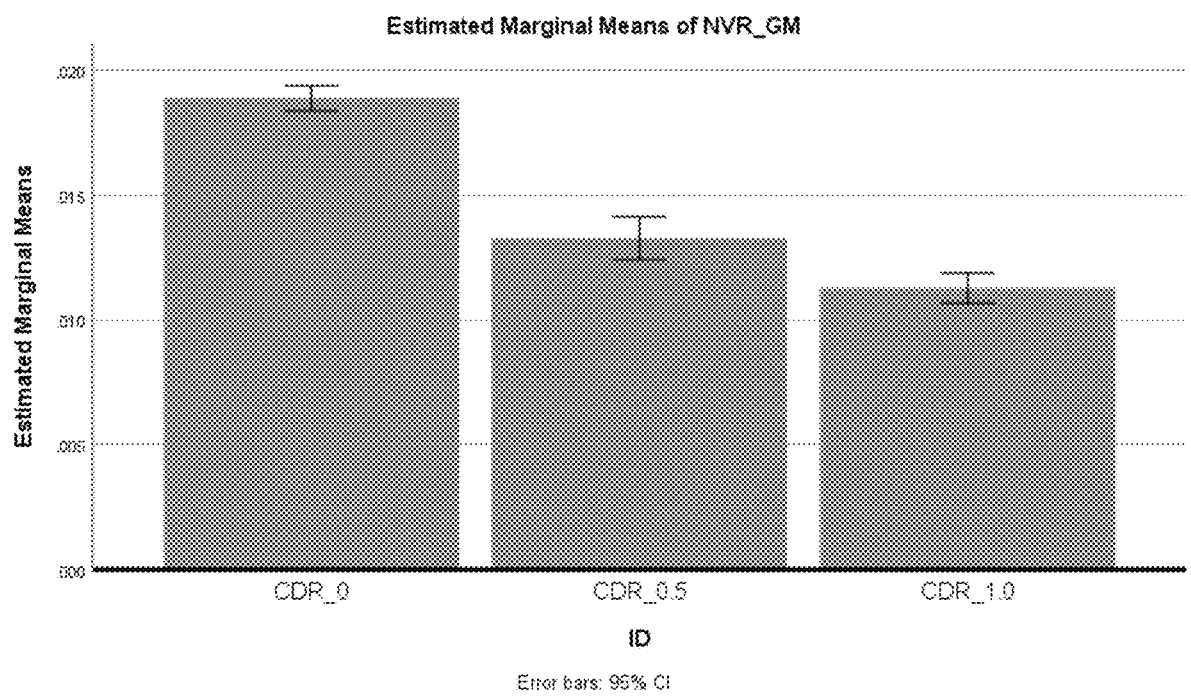
FIG. 5 shows results for patients with CDR 0, CDR 0.5, and CDR 1 for grey matter NVC.
Figure 6:
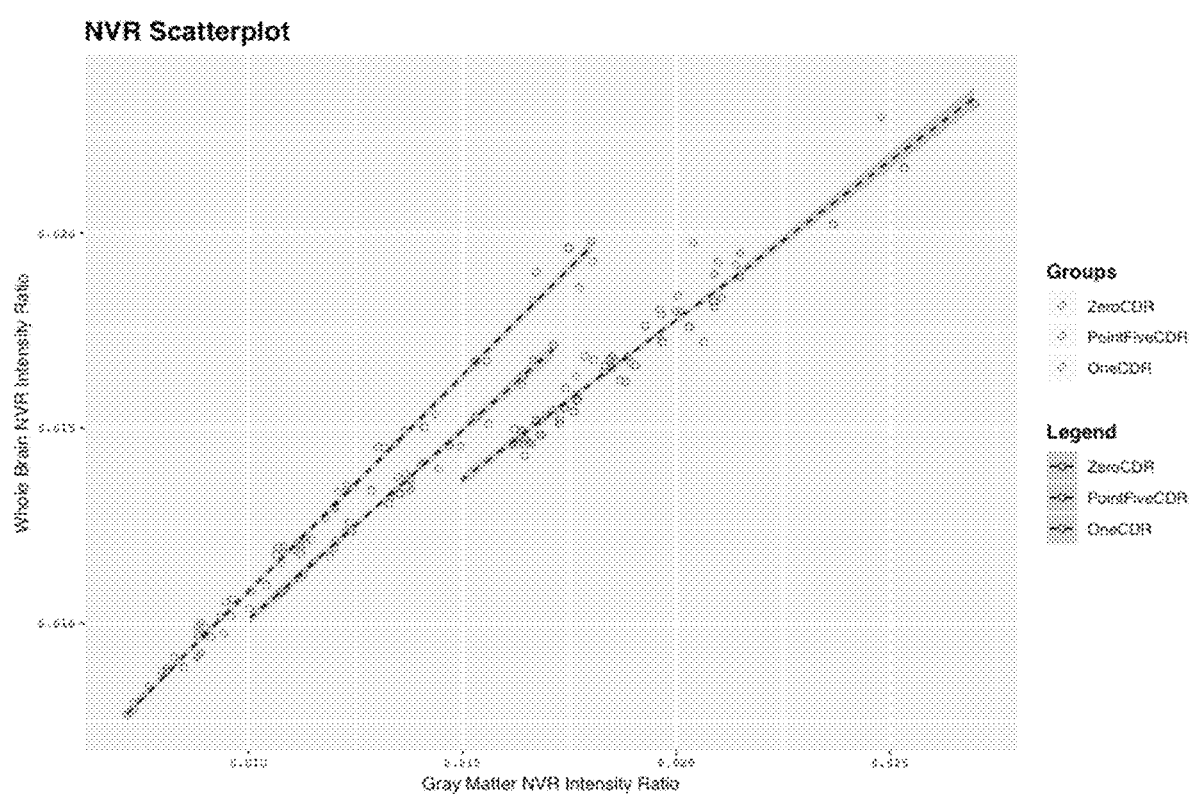
FIG. 6 shows results for patients with CDR 0, CDR 0.5, and CDR 1 for grey matter NVC and whole brain NVC.

Univariate analysis of variance (ANOVA) was computed to assess differences in white matter NVC and grey matter NVC between patients with CDR0, CDR0.5 and CDR1. As seen in FIG. 4, CDR0 group (mean=0.017, sd=0.002) has significantly higher [$F(2, 201)=75.77$, $p<0.0001$, partial-$\eta^2=0.43$] white matter NVC than CDR0.5 (mean=0.013, sd=0.0018) and the CDR1 groups (mean=0.012, sd=0.0033). The CDR0.5 group also had a higher white matter NVC than the CDR1 group (mean difference=0.001, sd=0.00052, $p<0.05$). As seen in FIG. 5, CDR0 group (mean=0.019, sd=0.0024) has significantly higher [$F(2, 201)=194.09$, $p<0.0001$, partial-$\eta^2=0.664$] grey matter NVC than CDR0.5 (mean=0.013, sd=0.0018) and than CDR1 (mean=0.011, st. dev=0.0030). CDR0.5 group also had significantly higher grey matter NVC than the CDR1 group (mean difference=0.002, st. dev=0.0005, $p<0.05$). FIG. 6 depicts the observable relationship between whole brain NVC and grey matter NVC across patients categorized as CDR 0, CDR 0.5, and CDR 1.

Permutation-based discriminant function analyses were used to determine the success with which NVC (white matter, grey matter or both) could be used to accurately classify participants according to their CDR rating. Surprisingly, using white matter NVC only, discriminant function analysis successfully differentiated between CDR0, CDR0.5 and CDR1 groups 68.7% of the time. Table 6 depicts detailed results.

TABLE 6

Classification Results[a]

| | ID | CDR_0 | CDR_0.5 | CDR_1.0 | Total |
|---|---|---|---|---|---|
| Original Count | CDR_0 | 78 | 21 | 0 | 99 |
| | CDR_0.5 | 5 | 16 | 13 | 34 |
| | CDR_1.0 | 12 | 12 | 44 | 68 |
| % | CDR_0 | 78.8 | 21.2 | .0 | 100.0 |
| | CDR_0.5 | 14.7 | 47.1 | 38.2 | 100.0 |
| | CDR_1.0 | 17.6 | 17.6 | 64.7 | 100.0 |

Surprisingly, using grey matter NVC only, discriminant function analysis successfully differentiated between CDR0, CDR0.5 and CDR1 groups 81.6% of the time. Table 7 depicts detailed results.

TABLE 7

Classification Results[a]

| | ID | CDR_0 | CDR_0.5 | CDR_1.0 | Total |
|---|---|---|---|---|---|
| Original Count | CDR_0 | 97 | 2 | 0 | 99 |
| | CDR_0.5 | 4 | 19 | 11 | 34 |
| | CDR_1.0 | 7 | 13 | 48 | 68 |
| % | CDR_0 | 98.0 | 2.0 | .0 | 100.0 |
| | CDR_0.5 | 11.8 | 55.9 | 32.4 | 100.0 |
| | CDR_1.0 | 10.3 | 19.1 | 70.6 | 100.0 |

Surprisingly, using white matter NVC and grey matter NVC, discriminant function analysis successfully differentiated between CDR0, CDR0.5 and CDR1 groups 96.5% of the time. Table 8 depicts detailed results.

Classification Results[a]

| | ID | CDR_0 | CDR_0.5 | CDR_1.0 | Total |
|---|---|---|---|---|---|
| Original Count | CDR_0 | 96 | 3 | 0 | 99 |
| | CDR_0.5 | 0 | 32 | 2 | 34 |
| | CDR_1.0 | 0 | 2 | 66 | 68 |
| % | CDR_0 | 97.0 | 3.0 | .0 | 100.0 |
| | CDR_0.5 | .0 | 94.1 | 5.9 | 100.0 |
| | CDR_1.0 | .0 | 2.9 | 97.1 | 100.0 |

[a]96.5% of original grouped cases correctly classified.

The description includes information that may be useful in understanding the present invention. It is not an admission that any of the information provided herein is prior art, necessary, or relevant to the presently claimed invention, or that any publication specifically or implicitly referenced is prior art.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be noted that any language directed to a computer device or a computer system should be read to include any suitable combination of computing devices, including servers, interfaces, systems, databases, agents, peers, engines, controllers, or other types of computing devices operating individually or collectively in a networked environment (e.g. local intranet or an Internet cloud). One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

The discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A system for analyzing a substrate-dependent activity in a brain tissue related to a condition, comprising:
   a scanner, wherein the scanner detects a plurality of signals related to the substrate-dependent activity in the brain tissue; and
   a computer processor informationally coupled to the scanner;
   wherein the computer processor:
      organizes the plurality of signals into a data set comprising a plurality of voxels;
      derives, within the data set, (1) a maximum value of a voxel from the Circle of Willis or the Vein of Galen and (2) a minimum value of a voxel from the Sagittal Sinus or the Middle Cerebral Artery, wherein the computer processor motion corrects the data set prior to deriving the maximum and minimum values, wherein the motion correcting comprises subsampling the data set for a local minima to identify an area in the data set having an absolute minima, followed by searching the area at higher resolution to identify the absolute minima;
      uses the maximum value and the minimum value to determine a plausible signal variability range of the plurality of voxels; and
      uses the plausible signal variability range in part to normalize at least some of the values in the data set.

2. The system of claim 1, wherein the computer processor further removes artifactual signals that arise from motion using motion parameters gathered from motion correction.

3. The system of claim 1, wherein the substrate-dependent activity is blood-oxygen-level dependent (BOLD).

4. The system of claim 1, wherein the scanner is a functional magnetic resonance imager (fMRI).

5. The system of claim 1, wherein the plurality of signals comprise the same type of signal.

6. The system of claim 1, wherein the plurality of signals comprise at least two different types of signal.

7. The system of claim 1, wherein the motion correcting comprises subsampling the data set for a local minima to identify an area in the data set of absolute minima, and applying a motion correction from a first portion of the data set to a second portion of the data set, wherein the second portion of the data set is successive to the first portion of the data set.

8. The system of claim 1, wherein the maximum value is derived from the Vein of Galen, and wherein the minimum value is derived from the Sagittal Sinus.

9. The system of claim 1, wherein the data set comprises a plurality of voxels.

10. The system of claim 9, wherein the maximum value is the mean of resting BOLD values from a first subset of voxels in the Vein of Galen, and wherein the minimum value is the mean of resting BOLD values from a second subset of voxels in the Sagittal Sinus.

11. The system of claim 1, wherein the maximum value and the minimum value define a plausible range of values, and wherein the computer processor uses the plausible range of values to normalize the data set.

12. The system of claim 1, wherein the maximum value is derived from the Circle of Willis, and wherein the minimum value is derived from the Sagittal Sinus.

13. The system of claim 1, wherein the maximum value is derived from the Circle of Willis, and wherein the minimum value is derived from the Middle Cerebral Artery.

14. The system of claim 1, wherein the maximum value is derived from the Vein of Galen, and wherein the minimum value is derived from the Middle Cerebral Artery.

15. The system of claim 1, further comprising a machine learning algorithm informationally coupled to the computer processor, wherein the machine learning algorithm is trained on the normalized values in the data set in order to classify the condition.

16. A system for analyzing a substrate-dependent activity in a brain tissue related to a condition, comprising:
   a scanner, wherein the scanner detects a plurality of signals related to the substrate-dependent activity in the brain tissue; and a computer processor informationally coupled to the scanner;

wherein the computer processor;

organizes the plurality of signals into a data set comprising a plurality of voxels;

derives, within the data set, (1) a maximum value of a voxel from the Circle of Willis or the Vein of Galen and (2) a minimum value of a voxel from the Sagittal Sinus or the Middle Cerebral Artery;

uses the maximum value and the minimum value to determine a plausible signal variability range of the plurality of voxels; and uses the plausible signal variability range in part to normalize at least some of the values in the data set by (i) determining a time series range for a voxel from the plurality of voxels, (ii) dividing the time series range by a plausible range for the voxel to derive a voxelwise variability ratio, and (iii) applying the voxelwise variability ratio to the data set.

17. A system for analyzing a substrate-dependent activity in a brain tissue related to a condition, comprising:

a scanner, wherein the scanner detects a plurality of signals related to the substrate-dependent activity in the brain tissue; and a computer processor informationally coupled to the scanner;

wherein the computer processor;

organizes the plurality of signals into a data set comprising a plurality of voxels:

derives, within the data set, (1) a maximum value of a voxel from the Circle of Willis or the Vein of Galen and (2) a minimum value of a voxel from the Sagittal Sinus or the Middle Cerebral Artery;

uses the maximum value and the minimum value to determine a plausible signal variability range of the plurality of voxels; and uses the plausible signal variability range in part to normalize at least some of the values in the data set by (i) determining a plausible signal variability of the voxel by subtracting the square of a standard deviation of the minimum value for the voxel from the square of a standard deviation of the maximum value of the voxel, (ii) dividing a time series variance of the voxel by the plausible signal variability for the voxel to derive a voxelwise plausible variance ratio, and (iii) applying the voxelwise plausible variance ratio to the data set.

\* \* \* \* \*